US011478185B2

(12) United States Patent
Kaikenger et al.

(10) Patent No.: US 11,478,185 B2
(45) Date of Patent: Oct. 25, 2022

(54) SKIN DRESSING HAVING SENSOR FOR PRESSURE ULCER PREVENTION

(71) Applicant: Hill-Rom Services, Inc., Batesville, IN (US)

(72) Inventors: Philippe Kaikenger, Pluvigner (FR); Michael Churilla, Harrison, OH (US); Frank E. Sauser, Cincinnati, OH (US); Charles A. Lachenbruch, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 259 days.

(21) Appl. No.: 16/743,089

(22) Filed: Jan. 15, 2020

(65) Prior Publication Data

US 2020/0253539 A1 Aug. 13, 2020

Related U.S. Application Data

(60) Provisional application No. 62/804,317, filed on Feb. 12, 2019.

(51) Int. Cl.
*A61B 5/00* (2006.01)

(52) U.S. Cl.
CPC ............ *A61B 5/447* (2013.01); *A61B 5/0004* (2013.01); *A61B 5/6811* (2013.01); *A61B 5/746* (2013.01); *A61B 2562/0261* (2013.01); *A61B 2562/04* (2013.01); *A61B 2562/164* (2013.01); *A61B 2562/168* (2013.01)

(58) Field of Classification Search
CPC .............. A61B 5/447; A61B 5/6801; A61B 5/6811–6812; A61B 2562/0261; A61B 2562/164
See application file for complete search history.

(56) References Cited

U.S. PATENT DOCUMENTS

| | | | |
|---|---|---|---|
| 3,304,528 A | 2/1967 | Rastrelli et al. |
| 3,789,511 A | 2/1974 | Groom et al. |
| 4,014,217 A | 3/1977 | Lagasse et al. |
| 4,492,949 A | 1/1985 | Peterson et al. |
| 4,547,668 A | 10/1985 | Tsikos |
| 4,570,354 A | 2/1986 | Hindes |

(Continued)

FOREIGN PATENT DOCUMENTS

CN 108403352 A 8/2018

OTHER PUBLICATIONS

Crivello, Matthew D. Thesis for the Degree of Master Science in Electrical and Computer Engineering, "Flexible Sensor for Measurement of Skin Pressure and Temperature for the Prevention of Pressure Ulcers," Worcester Polytechnic Institute, Oct. 2016, 113 pages.

*Primary Examiner* — Daniel L Cerioni
*Assistant Examiner* — Raymond P Dulman
(74) *Attorney, Agent, or Firm* — Barnes & Thornburg LLP

(57) ABSTRACT

A system for detecting pressure sores includes an artificial skin configured to be coupled to a patient's skin. The artificial skin includes a substrate and a strain sensor configured to detect deformation of the substrate. A transmitter is configured to transmit signals indicative of the deformation of the substrate. A control system is configured to receive the signals from the transmitter. The control system includes a timer to track a period of time that the substrate is deformed.

20 Claims, 11 Drawing Sheets

(56) References Cited

U.S. PATENT DOCUMENTS

| | | |
|---|---|---|
| 4,588,348 A | 5/1986 | Beni et al. |
| 4,668,861 A | 5/1987 | White |
| 4,682,608 A | 7/1987 | De Rigal et al. |
| 5,313,840 A | 5/1994 | Chen et al. |
| 5,333,217 A | 7/1994 | Kossat |
| 5,341,687 A | 8/1994 | Stan |
| 5,442,729 A | 8/1995 | Kramer et al. |
| 5,442,799 A | 8/1995 | Murakami et al. |
| 5,553,500 A | 9/1996 | Grahn et al. |
| 5,610,528 A | 3/1997 | Neely et al. |
| 5,672,979 A | 9/1997 | Christopher |
| 5,828,798 A | 10/1998 | Hopenfeld |
| 5,886,615 A | 3/1999 | Burgess |
| 5,917,165 A | 6/1999 | Platt et al. |
| 5,959,863 A | 9/1999 | Hoyt et al. |
| 6,071,819 A | 6/2000 | Yu-Chong et al. |
| 6,414,674 B1 | 7/2002 | Kamper et al. |
| 6,458,109 B1 | 10/2002 | Henley et al. |
| 6,825,539 B2 | 11/2004 | Tai et al. |
| 6,915,701 B1 | 7/2005 | Tarler |
| 6,951,143 B1 | 10/2005 | Adderton et al. |
| 6,953,982 B1 | 10/2005 | Tai et al. |
| 7,090,647 B2 | 8/2006 | Mimura et al. |
| 7,295,724 B2 | 11/2007 | Wang et al. |
| 7,500,399 B2 | 3/2009 | Cheng et al. |
| 7,658,119 B2 | 2/2010 | Loeb et al. |
| 7,815,998 B2 | 10/2010 | Simpson et al. |
| 7,854,173 B2 | 12/2010 | Cheng et al. |
| 7,878,075 B2 | 2/2011 | Johansson et al. |
| 8,033,189 B2 | 10/2011 | Hayakawa et al. |
| 8,316,719 B2 | 11/2012 | Majidi et al. |
| 9,277,829 B2 | 3/2016 | Jacofsky et al. |
| 9,711,029 B2 | 7/2017 | Ribble et al. |
| 9,778,131 B2 | 10/2017 | Everett et al. |
| 9,841,331 B2 | 12/2017 | Wood et al. |
| 10,251,593 B2 | 4/2019 | Sugla et al. |
| 10,638,969 B2 | 5/2020 | Drennan |
| 2005/0076715 A1 | 4/2005 | Kuklis et al. |
| 2005/0160827 A1 | 7/2005 | Zdeblick et al. |
| 2005/0165284 A1* | 7/2005 | Gefen ............... A61B 5/6804 600/300 |
| 2005/0261632 A1 | 11/2005 | Xu |
| 2008/0012582 A1* | 1/2008 | Jang ............... A61B 5/0531 324/692 |
| 2008/0087069 A1 | 4/2008 | Renken et al. |
| 2008/0087105 A1 | 4/2008 | Renken et al. |
| 2008/0108122 A1 | 5/2008 | Paul et al. |
| 2009/0098521 A1 | 4/2009 | Kuo et al. |
| 2009/0272201 A1 | 11/2009 | Loeb et al. |
| 2010/0132476 A1 | 6/2010 | Cheng et al. |
| 2011/0004276 A1* | 1/2011 | Blair ............... A61B 90/90 607/60 |
| 2011/0096327 A1 | 4/2011 | Papautsky et al. |
| 2011/0132871 A1 | 6/2011 | White et al. |
| 2011/0157088 A1 | 6/2011 | Motomura et al. |
| 2011/0193363 A1 | 8/2011 | Nishiwaki |
| 2013/0170218 A1 | 7/2013 | Wolk et al. |
| 2014/0238153 A1 | 8/2014 | Wood et al. |
| 2015/0088043 A1 | 3/2015 | Goldfield et al. |
| 2017/0027498 A1* | 2/2017 | Larson ............... A61B 5/002 |
| 2017/0281073 A1 | 10/2017 | Drennan et al. |
| 2018/0303407 A1 | 10/2018 | Jia et al. |
| 2019/0021650 A1 | 1/2019 | Lee et al. |
| 2019/0290496 A1 | 9/2019 | Brownhill et al. |

* cited by examiner

SKIN DRESSING HAVING SENSOR FOR PRESSURE ULCER PREVENTION

CROSS-REFERENCE TO RELATED APPLICATIONS

This application claims priority under 35 U.S.C. § 119(e) to U.S. Provisional Patent Application Ser. No. 62/804,317, filed Feb. 12, 2019, which is expressly incorporated by reference herein.

BACKGROUND

The present disclosure relates to pressure sore prevention, and more particularly, to a method of using an artificial skin for monitoring patient anatomy sites that are at risk for developing pressure sores.

A pressure ulcer typically develops due to a lack of tissue vascularization, which is associated with pressure over time. Tissue deformation is a more relevant physical measurement than pressure to detect that tissue geometry has changed and blood vessels may be pinched. Therefore, caregivers may welcome dressings that are applied on parts of the body which are more prone to pressure ulcers (sacrum area, shoulder, heel, elbow) and that could help to detect that the tissue has been compressed or deformed for too long a period of time.

SUMMARY

The present disclosure includes one or more of the features recited in the appended claims and/or the following features which, alone or in any combination, may comprise patentable subject matter.

According to an aspect of the disclosed embodiments, a system for detecting pressure sores includes an artificial skin that may be configured to be coupled to a patient's skin. The artificial skin may include a substrate and a strain sensor configured to detect deformation of the substrate. A transmitter may be configured to transmit signals indicative of the deformation of the substrate. A control system may be configured to receive the signals from the transmitter. The control system may have a timer to track a period of time that the substrate is deformed. The control system may compare the period of time that the substrate is deformed to a predetermined time. The control system may activate an alert if the period of time that the substrate is deformed is greater than the predetermined time.

In some embodiments, the artificial skin may be configured to be coupled to a patient's healthy skin. The artificial skin may be configured to be coupled to a patient's healthy skin in regions that are prone to pressure sores.

Optionally, the artificial skin may include at least one deformation axis. The strain sensor may detect deformation of the substrate along the deformation axis. The artificial skin may have a first strain sensor that may detect deformation of the substrate along a first deformation axis. A second strain sensor may detect deformation of the substrate along a second deformation axis. The first deformation axis may be transverse to the second deformation axis. The artificial skin may include a pressure sensor that may detect deformation of the substrate along a third deformation axis. The third deformation axis may be transverse to the first deformation axis and the second deformation axis. The first deformation axis may be substantially perpendicular to the second deformation axis. The third deformation axis may be substantially perpendicular to the first deformation axis and the second deformation axis. The first deformation axis and the second deformation axis may extend along a surface of the patient's skin. The third deformation axis may extend substantially perpendicular to a surface of the patient's skin.

Alternatively or additionally, the alert may include at least one of a visual alert or an audible alert. The control system may transmit the alert to a remote device. The remote device may include a device at a nurse's station. The remote device may include a wearable device.

It may be desired that the strain sensor includes an elastic strain sensor. The elastic strain sensor may include a conductive liquid. The conductive liquid may include a conductive metal. The conductive liquid may include eutectic gallium-indium.

It is contemplated that the predetermined time may be selected based on a patient's skin type. The patient's skin type may include a dryness of the patient's skin. The predetermined time may be selected based on a location of the patient's skin where the artificial skin is placed. The location of the patient's skin may include locations prone to pressure sores.

In some embodiments, the transmitter may be a wireless transmitter. The strain sensor may detect deformation of the skin in at least one direction. The strain sensor may detect deformation of the skin in at least two directions. The strain sensor may detect deformation of the skin in at least three directions. Deformation of the substrate may be indicative of pressure sores developing.

According to another aspect of the disclosed embodiments, a system for detecting pressure sores may include an artificial skin that may configured to be coupled to a patient's skin. The artificial skin may include a substrate. A first strain sensor may be configured to detect deformation of the substrate along a first deformation axis that extends along a surface of the patient's skin. A second strain sensor may be configured to detect deformation of the substrate along a second deformation axis that extends along a surface of the patient's skin transverse to the first deformation axis. A transmitter may be configured to transmit signals indicative of the deformation of the substrate. A control system may be configured to receive the signals from the transmitter. The control system may have a timer to track a period of time that the substrate is deformed. The control system may compare the period of time that the substrate is deformed to a predetermined time. The control system may activate an alert if the period of time that the substrate is deformed is greater than the predetermined time.

In some embodiments, the artificial skin may include a pressure sensor to detect deformation of the substrate along a third deformation axis. The third deformation axis may be transverse to the first deformation axis and the second deformation axis. The first deformation axis may be substantially perpendicular to the second deformation axis. The third deformation axis may be substantially perpendicular to the first deformation axis and the second deformation axis. The third deformation axis may extend substantially perpendicular to a surface of the patient's skin.

Optionally, the artificial skin may be configured to be coupled to a patient's healthy skin. The artificial skin may be configured to be coupled to a patient's healthy skin in regions that are prone to pressure sores.

It may be desired that the alert includes at least one of a visual alert or an audible alert. The control system may transmit the alert to a remote device. The remote device may include a device at a nurse's station. The remote device may include a wearable device.

It is contemplated that each of the first strain sensor and the second strain sensor may include an elastic strain sensor. The elastic strain sensor may include a conductive liquid. The conductive liquid may include a conductive metal. The conductive liquid may include eutectic gallium-indium.

Alternatively or additionally, the predetermined time may be selected based on a patient's skin type. The patient's skin type may include a dryness of the patient's skin. The predetermined time may be selected based on a location of the patient's skin where the artificial skin is placed. The location of the patient's skin may include locations prone to pressure sores. Deformation of the substrate may be indicative of pressure sores developing. Optionally, the transmitter may be a wireless transmitter.

According to a further aspect of the disclosed embodiments, a system for detecting pressure sores may include an artificial skin configured to be coupled to a patient's skin. The artificial skin may include a substrate. A first strain sensor may be configured to detect deformation of the substrate along a first deformation axis that extends along a surface of the patient's skin. A second strain sensor may be configured to detect deformation of the substrate along a second deformation axis that extends along a surface of the patient's skin substantially perpendicular to the first deformation axis. A pressure sensor may be configured to detect deformation of the substrate along a third deformation axis that extends substantially perpendicular to the first deformation axis and the second deformation axis. A transmitter may be configured to transmit signals indicative of the deformation of the substrate. A control system may be configured to receive the signals from the transmitter. The control system may have a timer to track a period of time that the substrate is deformed. The control system may compare the period of time that the substrate is deformed to a predetermined time. The control system may activate an alert if the period of time that the substrate is deformed is greater than the predetermined time. Alternatively or additionally, the third deformation axis may extend substantially perpendicular to a surface of the patient's skin.

Optionally, the artificial skin may be configured to be coupled to a patient's healthy skin. The artificial skin may be configured to be coupled to a patient's healthy skin in regions that are prone to pressure sores.

It may be desired that the alert includes at least one of a visual alert or an audible alert. The control system may transmit the alert to a remote device. The remote device may include a device at a nurse's station. The remote device may include a wearable device.

In some embodiments, each of the first strain sensor, the second strain sensor, and the pressure sensor may include an elastic strain sensor. The elastic strain sensor may include a conductive liquid. The conductive liquid may include a conductive metal. The conductive liquid may include eutectic gallium-indium.

It is contemplated that the predetermined time may be selected based on a patient's skin type. The patient's skin type may include a dryness of the patient's skin. The predetermined time may be selected based on a location of the patient's skin where the artificial skin is placed. The location of the patient's skin may include locations prone to pressure sores. Deformation of the substrate may be indicative of pressure sores developing. In some embodiments, the transmitter may be a wireless transmitter.

According to an aspect of the disclosed embodiments, a system for detecting pressure sores may include an artificial skin that may be configured to be coupled to a patient's skin. The artificial skin may include a substrate and a plurality strain sensors. Each of the plurality of strain sensors may be configured to detect deformation of the substrate along a different deformation axis. A transmitter may be configured to transmit signals indicative of the deformation of the substrate. A control system may be configured to receive the signals from the transmitter. The control system may have a timer to track a period of time that the substrate is deformed. The control system may compare the period of time that the substrate is deformed to a predetermined time. The control system may activate an alert if the period of time that the substrate is deformed is greater than the predetermined time.

Alternatively or additionally, at least one of the plurality of strain sensors may detect deformation of the substrate along a deformation axis that extends transverse to a surface of the patient's skin. At least one of the plurality of strain sensors may detect deformation of the substrate along a deformation axis that extends along a surface of the patient's skin.

In some embodiments, the artificial skin may be configured to be coupled to a patient's healthy skin. The artificial skin may be configured to be coupled to a patient's healthy skin in regions that are prone to pressure sores.

Optionally, the alert may include at least one of a visual alert or an audible alert. The control system may transmit the alert to a remote device. The remote device may include a device at a nurse's station. The remote device may include a wearable device.

It may be desired that each of the plurality of strain sensors includes an elastic strain sensor. The elastic strain sensor may include a conductive liquid. The conductive liquid may include a conductive metal. The conductive liquid may include eutectic gallium-indium.

It is contemplated that the predetermined time may be selected based on a patient's skin type. The patient's skin type may include a dryness of the patient's skin. The predetermined time may be selected based on a location of the patient's skin where the artificial skin is placed. The location of the patient's skin may include locations prone to pressure sores.

In some embodiments, the transmitter may be a wireless transmitter. Optionally, deformation of the substrate may be indicative of pressure sores developing.

According to another aspect of the disclosed embodiments, a method of detecting pressure sores may include coupling an artificial skin to a patient's healthy skin. The artificial skin may include a substrate and a plurality strain sensors each configured to detect deformation of the substrate along a different deformation axis. The method may also include detecting deformation of the substrate along at least one deformation axis. The method may also include transmitting signals indicative of the deformation of the substrate to a control system. The method may also include tracking a period of time that the substrate is deformed. The method may also include comparing the period of time that the substrate is deformed to a predetermined time. The method may also include activating an alert if the period of time that the substrate is deformed is greater than the predetermined time.

In some embodiments, detecting deformation of the substrate along at least one deformation axis may include detecting deformation of the substrate along a deformation axis that extends transverse to a surface of the patient's skin. Detecting deformation of the substrate along at least one deformation axis may include detecting deformation of the substrate along a deformation axis that extends along a surface of the patient's skin. Optionally, coupling an artificial skin to a patient's healthy skin may include coupling the artificial skin in regions that are prone to pressure sores.

It may be desired that activating an alert includes activating at least one of a visual alert or an audible alert. The method may also include transmitting the alert to a remote device. The remote device may include a device at a nurse's station. The remote device may include a wearable device.

In some embodiments, each of the plurality of strain sensors may include an elastic strain sensor. The elastic strain sensor may include a conductive liquid. The conductive liquid may include a conductive metal. The conductive liquid may include eutectic gallium-indium.

Optionally, the method may also include selecting the predetermined time based on a patient's skin type. The patient's skin type may include a dryness of the patient's skin. The method may also include selecting the predetermined time based on a location of the patient's skin where the artificial skin is placed. The location of the patient's skin may include locations prone to pressure sores.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Although this disclosure refers to specific embodiments, it will be understood by those skilled in the art that various changes in form and detail may be made without departing from the subject matter set forth in the accompanying claims.

Figure 1:
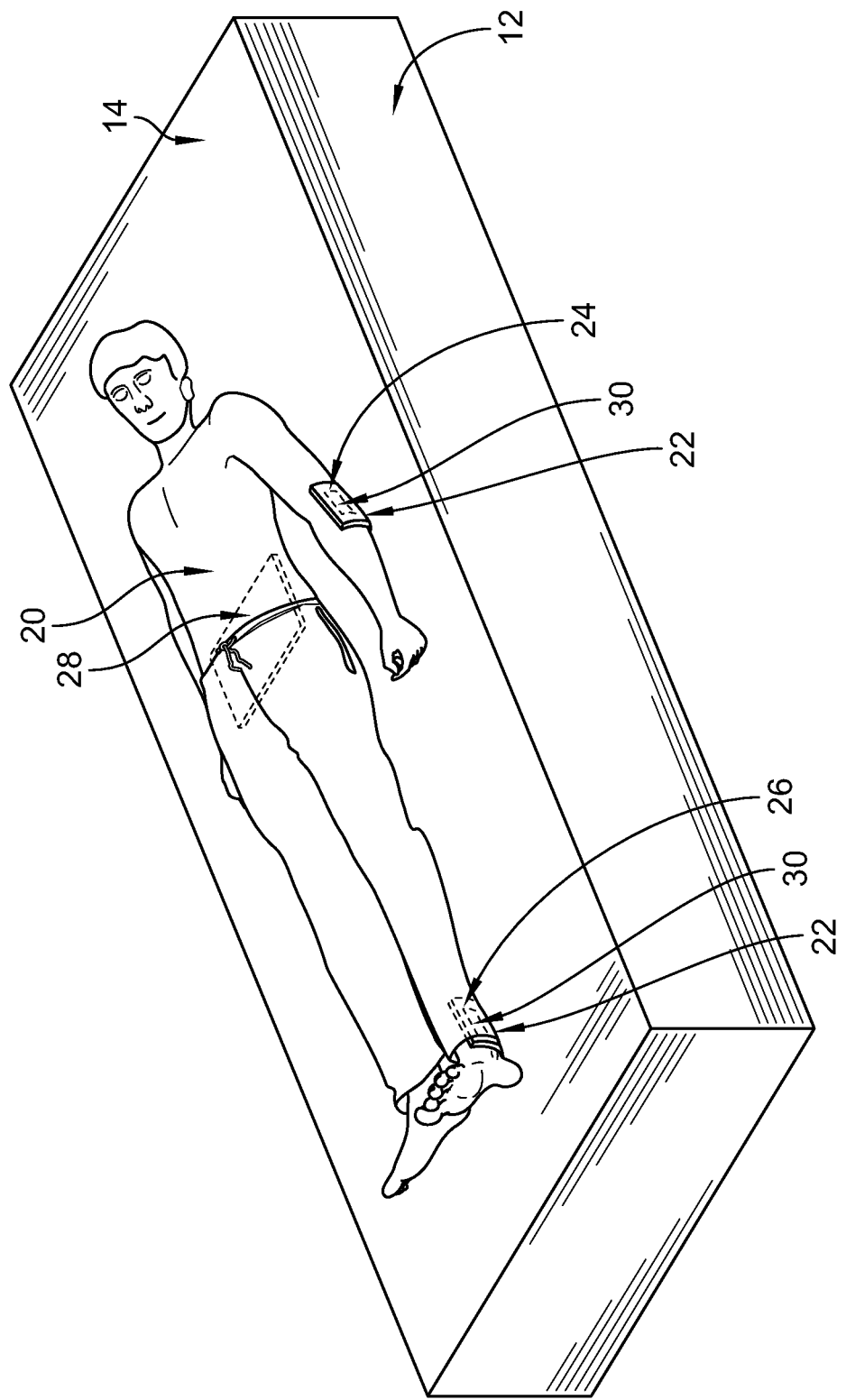
FIG. 1 is a side view of a patient support apparatus having a patient positioned thereon, wherein the patient is wearing artificial skin on areas of the patient's body that are susceptible to pressure sores.

Referring to FIG. 1, a patient support apparatus 10 is illustrated as a hospital bed 12 having a mattress 14. In other embodiments, the patient support apparatus 10 may be any apparatus for supporting a patient, for example, a chair, a wheelchair, a stretcher, a cot, or the like. A patient 20 is positioned on the apparatus 10. Artificial skin 22 having a strain sensor 30 is placed on the patient's skin. In an exemplary embodiment, the artificial skin 22 is placed on the patient's healthy skin at locations that are susceptible to pressure sores. For example, in the illustrated embodiment, the artificial skin 22 is positioned on the patient's elbow 24, heel 26, and sacrum 28. In other embodiments, the artificial skin 22 may be placed on any location of the patient's body, for example, other locations that are susceptible to pressure sores.

The artificial skin 22 is used to detect deformation of the patient's skin along multiple axes. As described below, the artificial skin 22 is configured to detect pressure and strains. The pressure and strains detected by the artificial skin correlates to deformation of the patient's skin. That is, as the patient's skin deforms, the deformation of the skin deforms the artificial skin 22. The deformation of the artificial skin 22 is measured as a pressure and strains. By monitoring the measured pressure and strains, an amount of skin deformation is calculated. Additionally, an amount of time that the skin is deformed is monitored. Accordingly, if the patient's skin has deformation that exceeds a predetermined threshold for a predetermined time, an alert is activated. In some embodiments, an amount of measured deformation is dependent on a type of skin of the patient, e.g. a dryness of the patient skin or oil on the patient's skin.

Figure 2:
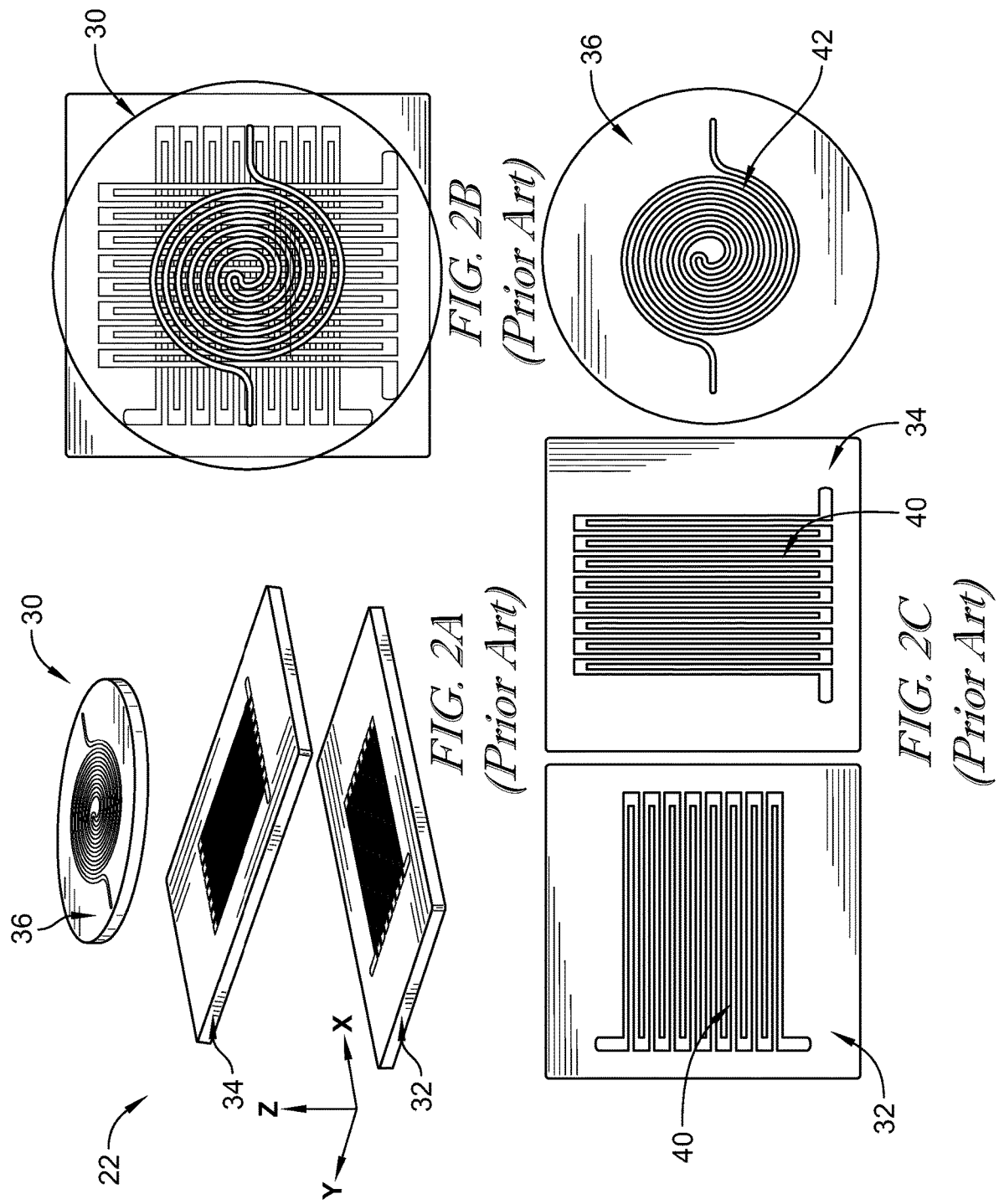
FIG. 2(a) is a perspective exploded view of the artificial skin, shown in FIG. 1, including an x-axis sensor that detects deformation along a first deformation axis, a y-axis sensor that detects deformation along a second deformation axis, and a z-axis sensor that detects deformation along a third deformation axis.
FIG. 2(b) is a top plan view of the artificial skin having the x-axis sensor, y-axis sensor, and z-axis sensor layered together.
FIG. 2(c) is a top plan view of the x-axis sensor, y-axis sensor, and z-axis sensor.

The artificial skin 22, may be as described in U.S. Pat. No. 9,841,331 issued to Wood, et al on Dec. 12, 2017, which is hereby incorporated herein by reference in its entirety. As shown in FIG. 2(a), a sensor 30 is used to sense strain in the X and Y dimension and pressure in the Z dimension. FIG. 2(b) shows a top view of the sensor 30, wherein the two unidirectional strain sensors, an x-axis strain sensor 32 and a y-axis strain sensor 34 are arranged with their strain axes orthogonal to provide strain sensing in the X and Y dimensions and a pressure sensor 36 is provided on the top layer to sense pressure in the Z dimension. FIG. 2(c) shows the individual layer patterns for the sensor 30.

Illustrative sensor 30 includes three soft sensor layers made of silicone rubber that have a modulus of elasticity of approximately 69 kPa and a shore hardness of approximately 00-30. The strain sensors 32, 34 include substantially similarly shaped straight-line microchannel patterns 40 that are sensitive to axial strains as well as to contact pressure. The pressure sensor 36 includes a circular pattern 42 for pressure sensing. An x-axis strain sensor 32 is placed on top of the y-axis strain sensor 34 with a 90 degree rotation for detecting strain along a substantially perpendicular axis. Using the combination of the signals from the three sensors 32, 34, and 36, the device 30 detects and distinguishes three different stimuli: x-axis strain, y-axis strain, and z-axis pressure. All three sensor layers are connected through interconnects between layers, making one circuit that is electrically equivalent to three variable resistors connected in series.

Figure 3:
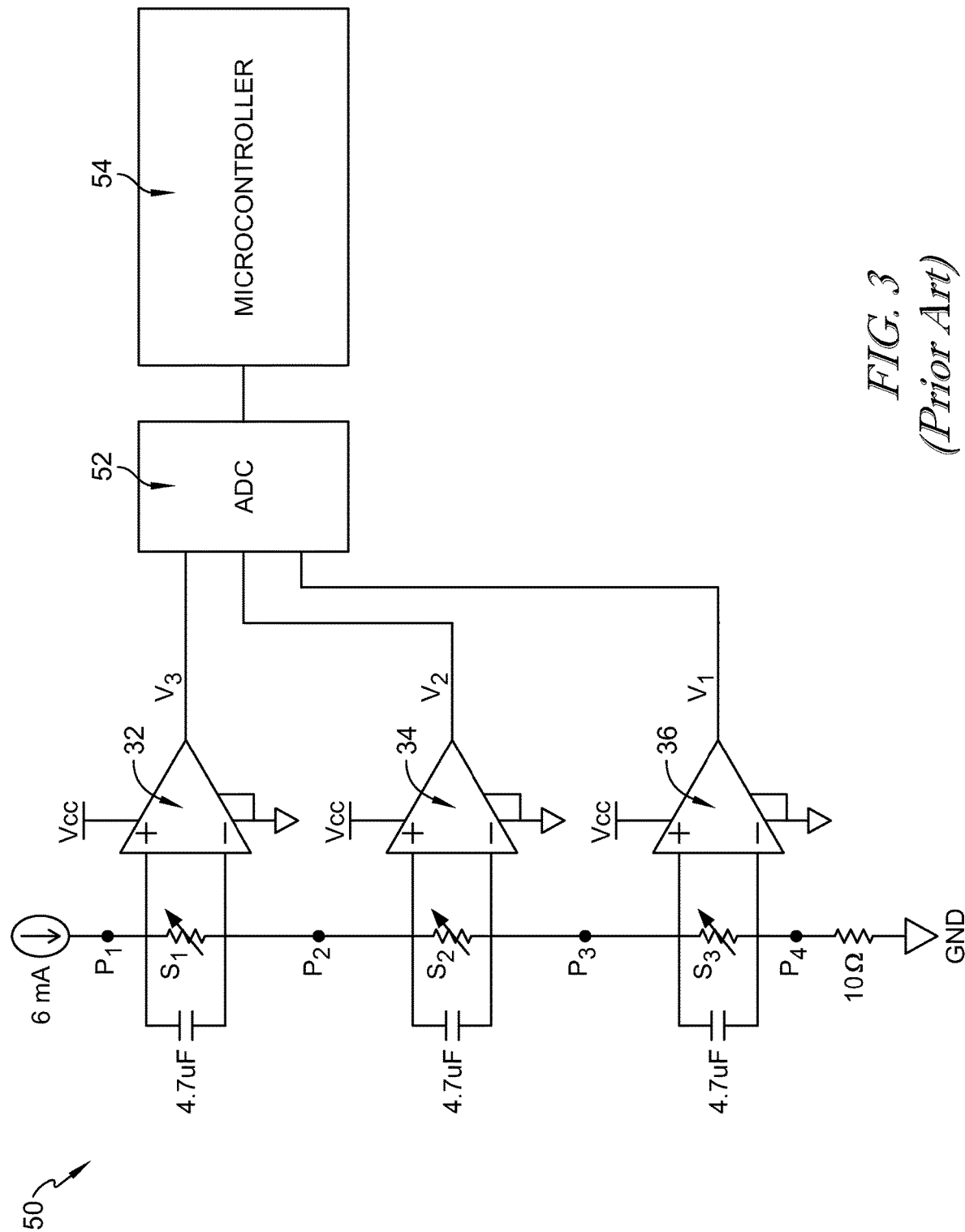
FIG. 3 is a circuit diagram of the artificial skin showing the electrical connections between the x-axis sensor, the y-axis sensor, and the z-axis sensor.

FIG. 3 illustrates the circuit diagram 50 that is used to read signals from the three sensor layers 32, 34, 36, in some embodiments. In other embodiments, different capacitor values and resistor values are used. A constant current source is used to generate constant current that flows through the three sensors 32, 34, 36 in series, creating voltage drops at each sensor layer. The voltage difference across each sensor is amplified by an instrumentation amplifier. The amplified signals are connected to three analog-to-digital conversion ports 52 of a microcontroller 54 to separately measure the resistance changes. The resistance changes are utilized to determine a pressure and strain on the sensor 30.

Figure 5:
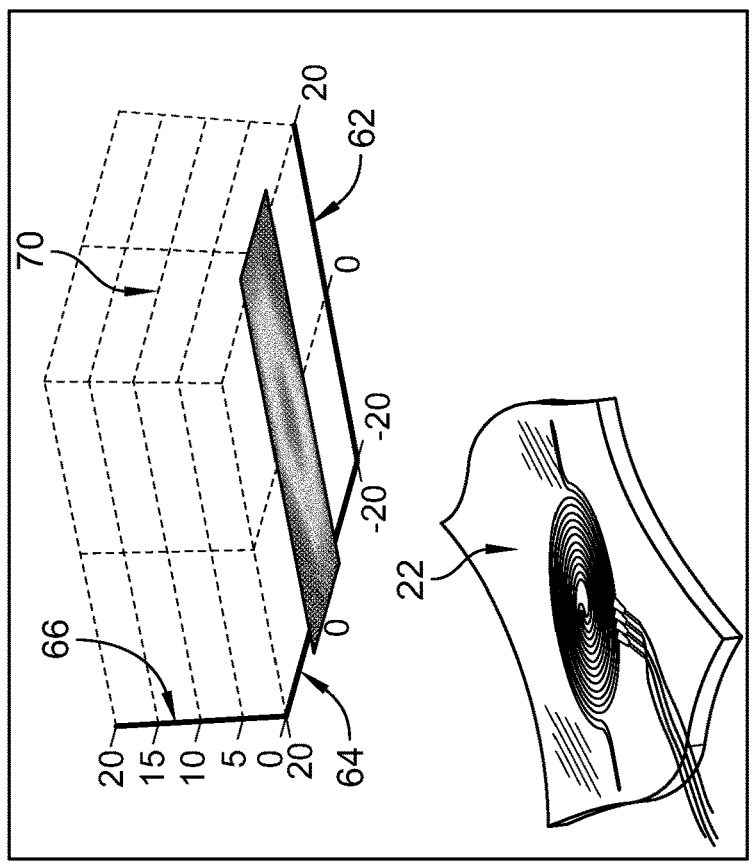
FIG. 5 is a perspective view of the artificial skin being deformed along the x-axis, and a graph illustrating the deformation detected by the artificial skin.
Figure 4:
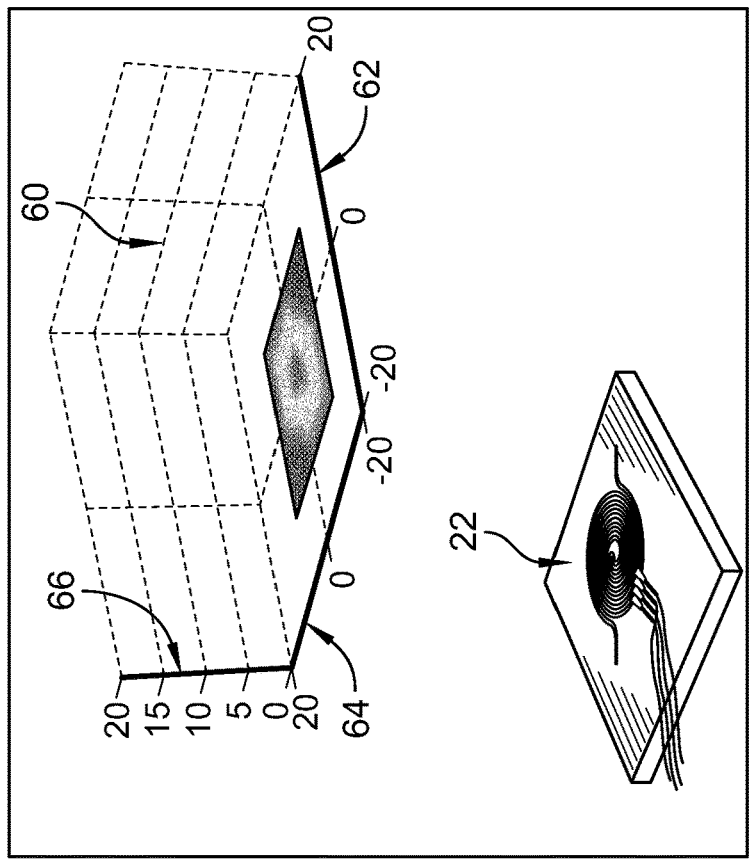
FIG. 4 is a perspective view of the artificial skin in a non-deformed state, and a graph illustrating the pressure detected by the artificial skin.
Figure 6:
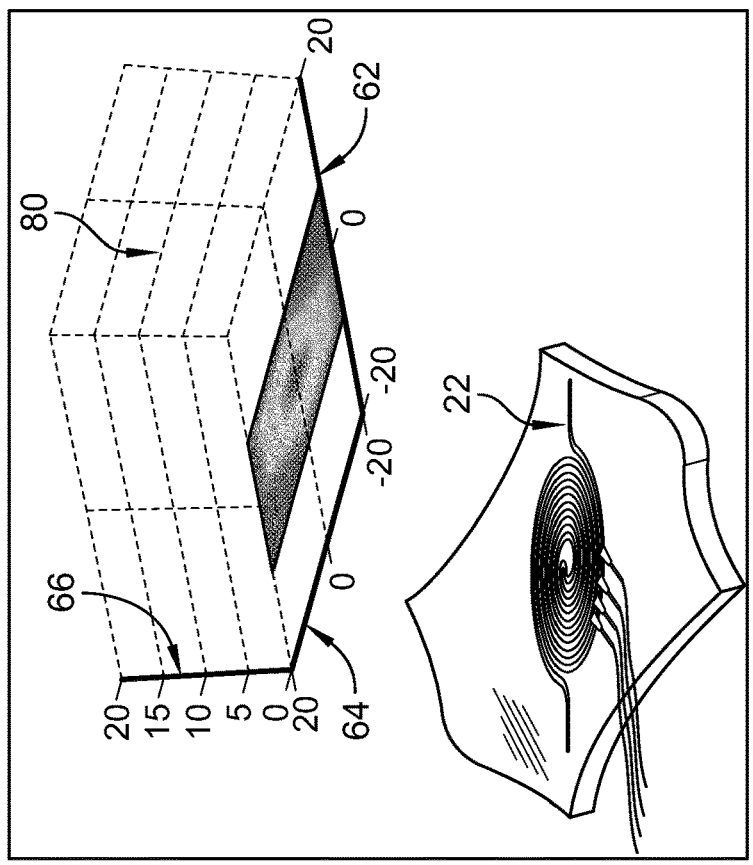
FIG. 6 is a perspective view of the artificial skin being deformed along the y-axis, and a graph illustrating the deformation detected by the artificial skin.

The detected pressure and strain correlates to a deformation of the patient's skin when the artificial skin 22 is attached to the patient's skin. FIG. 4 illustrates the artificial skin 22 in a non-deformed state. The graph 60 illustrates strain detected along the x-axis 62, strain detected along the y-axis 64, and pressure detected along the z-axis 66. In FIG. 5, the artificial skin 22 is stretched along the x-axis. The graph 70 shows that the strain detected along the x-axis 62 is increased. The strain detected by the x-axis sensor 32 correlates to deformation of the patient's skin along a first deformation axis, e.g. the x-axis. When the artificial skin 22 is applied to the patient's skin, the first deformation axis is substantially parallel to a surface of the patient's skin. In embodiments where the artificial skin 22 is applied to a curved portion of the patient's skin, the first deformation axis curves with and follows the contours of the patient's skin. In FIG. 6, the artificial skin 22 is stretched along the y-axis. The graph 80 shows that the strain detected along the y-axis 64 is increased. The strain detected by the y-axis sensor 34 correlates to deformation of the patient's skin along a second deformation axis, e.g. the y-axis. When the artificial skin 22 is applied to the patient's skin, the second deformation axis is substantially parallel to a surface of the patient's skin. In embodiments where the artificial skin 22 is applied to a curved portion of the patient's skin, the second deformation axis curves with and follows the contours of the patient's skin. The second deformation axis is substantially perpendicular to the first deformation axis in some embodiments, but non-orthogonal X and Y axis orientations are also contemplated by the present disclosure.

Figure 7:
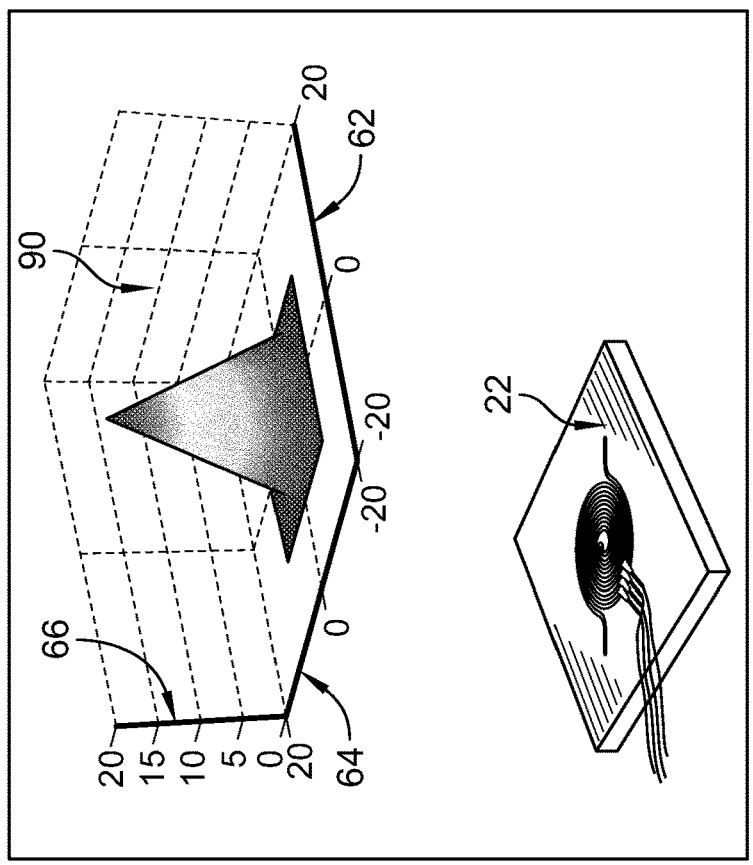
FIG. 7 is a perspective view of the artificial skin being deformed along the z-axis, and a graph illustrating the deformation detected by the artificial skin.

In FIG. 7, the artificial skin 22 is stretched along the z-axis. The illustrative z-axis stretching is due to compression of the artificial skin 22 in a downward direction in FIG. 7. The graph 90 shows that the pressure detected along the z-axis 66 is increased. The pressure detected by the pressure sensor 36 correlates to deformation of the patient's skin along a third deformation axis, e.g. the z-axis. When the artificial skin 22 is applied to the patient's skin, the third deformation axis is substantially perpendicular to a surface of the patient's skin. The third deformation axis is substantially perpendicular to both the first deformation axis and the second deformation axis in some embodiments, but non-orthogonal orientations third (z) axis relative to the first (x) axis and the second (y) axis are also contemplated by this disclosure.

Figure 8:
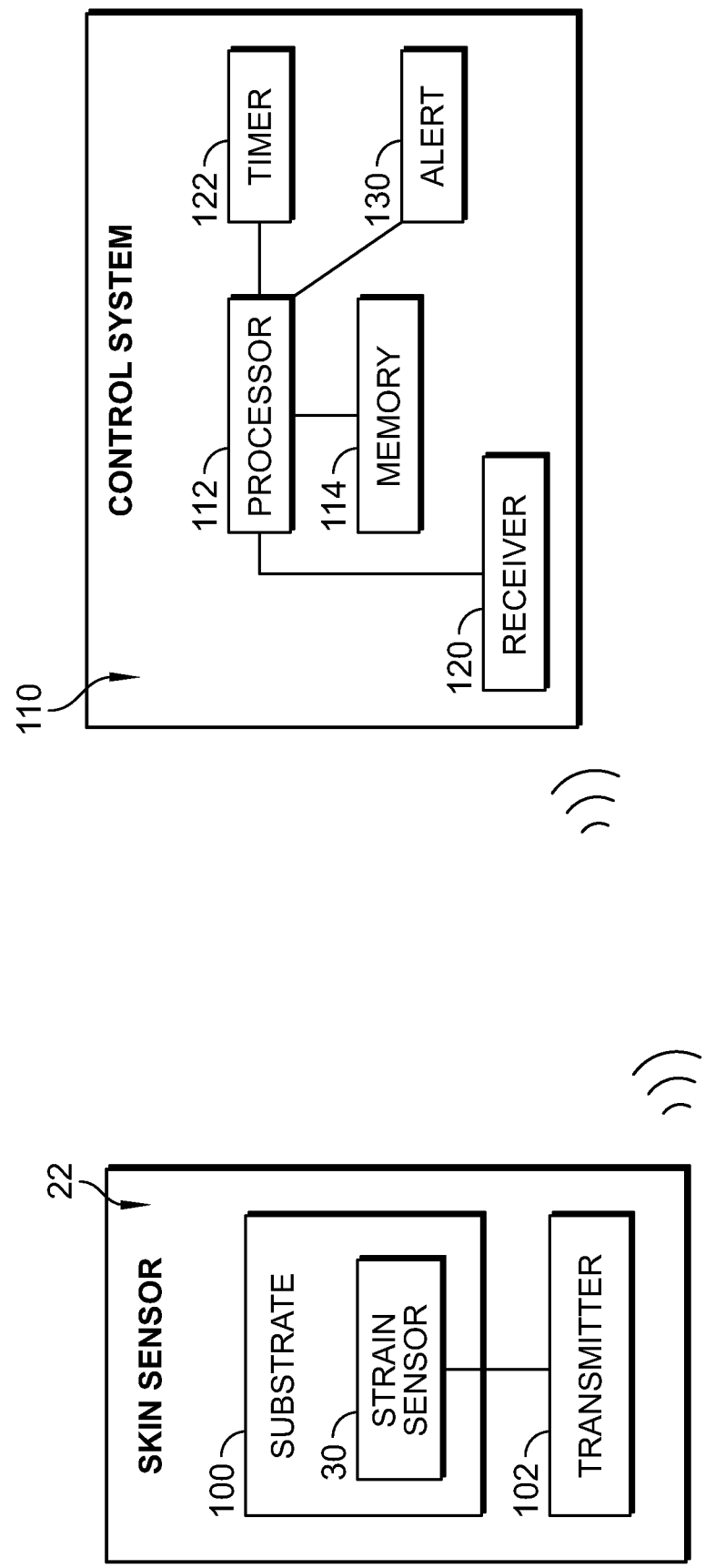
FIG. 8 is a block diagram of the artificial skin sensor in communication with a control system having a timer and an alert.

Referring now to FIG. 8, the artificial skin 22 includes a substrate 100 that is formed from silicon rubber in some embodiments. The sensors 32, 34, 36 are embedded within the substrate 100 and are simply depicted as strain sensor 30 in FIG. 8. In some embodiments, each of the sensors 32, 34, 36 includes a conductive liquid, for example, a conductive metal or eutectic gallium-indium. The sensor 30 detects signals from the sensors 32, 34, 36 to determine strain along the x-axis and y-axis and pressure along the z-axis, as described above. A transmitter 102 transmits these data correlating to these signals to a control system 110. In some embodiments, the artificial skin 22 is wired to the control system 110.

The control system 110 includes a processor 112, for example, a micro-processor that is electrically coupled to a memory 114. The memory 114 include instructions to be carried out by the processor 112. A transceiver or receiver 120 receives the data from the transmitter 102 and relays the data to the processor 112. The processor 112 is configured to correlate the detected strain and pressure to a deformation of the patient's skin along the x-axis, y-axis, and z-axis. A timer 122 tracks a period of time that the patient's skin is deformed. In some embodiments, if the deformation of the skin exceeds a predetermined threshold for a predetermined time, the processor 112 send a signal to an alert 130 that notifies a caregiver of the deformation of the patient's skin. The alert 130 may be an audible alert or a visual alert, for example, an alarm or a light.

Figure 9:
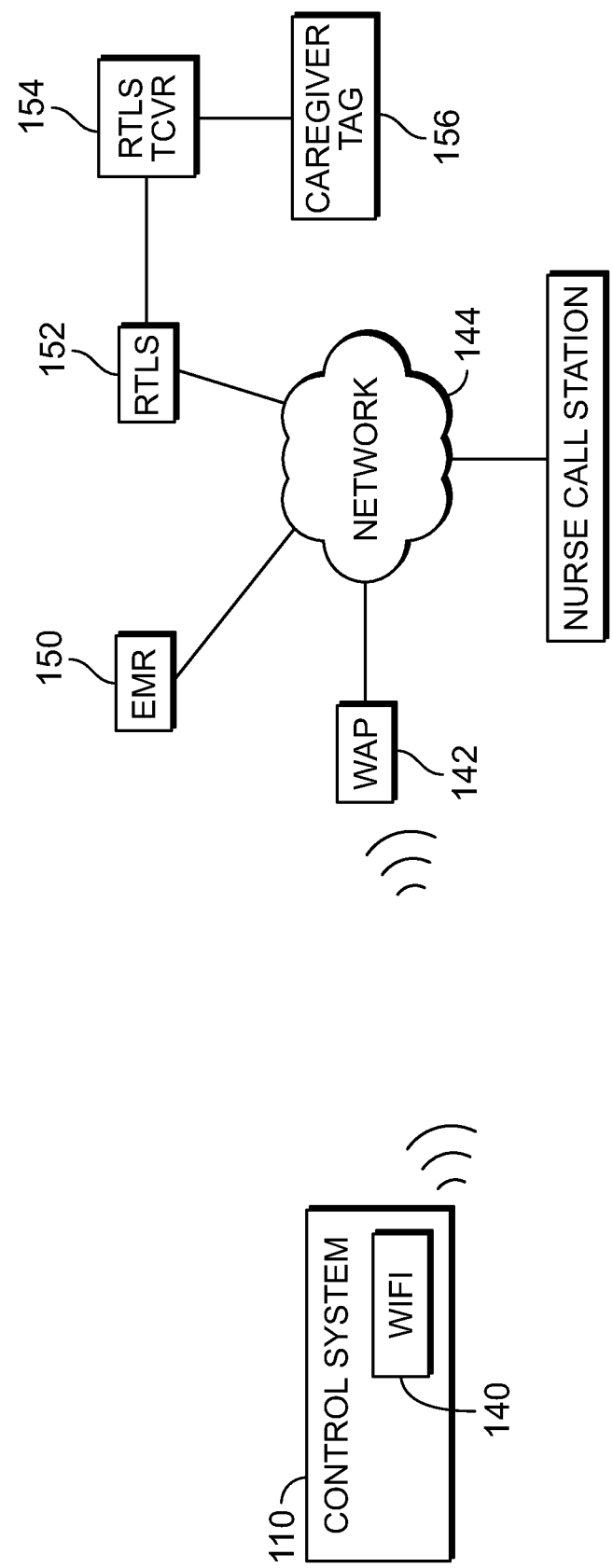
FIG. 9 is a block diagram of the control system shown in FIG. 8 in communication with a healthcare facility network that includes an electronic medical record, a real-time locating system, and a nurse call station.

Referring to FIG. 9, the control system 110 includes wireless capabilities 140 in some embodiments, such as having a WiFi module, to deliver signals to a wireless access point 142 of a healthcare facility network 144. In some embodiments, the control system 110 is wired to the network 144. The network 144 includes an electronic medical record 150 that may track and record the detected deformation of the patient's skin and any alerts pertaining thereto. Also, a real-time locating system 152 may be utilized to identify a caregiver close to the patient. A transceiver 154 of the real-time locating system 152 may transmit a signal to a caregiver tag 156 to notify the caregiver of an alert. For example, the caregiver tag 156 may be a wearable tag that notifies the caregiver in response to the deformation of the patient's skin exceed the predetermined threshold for the predetermined period of time. Likewise, the alert may be transmitted to a remote device 160, for example, a nurse's station 158.

Figure 10:
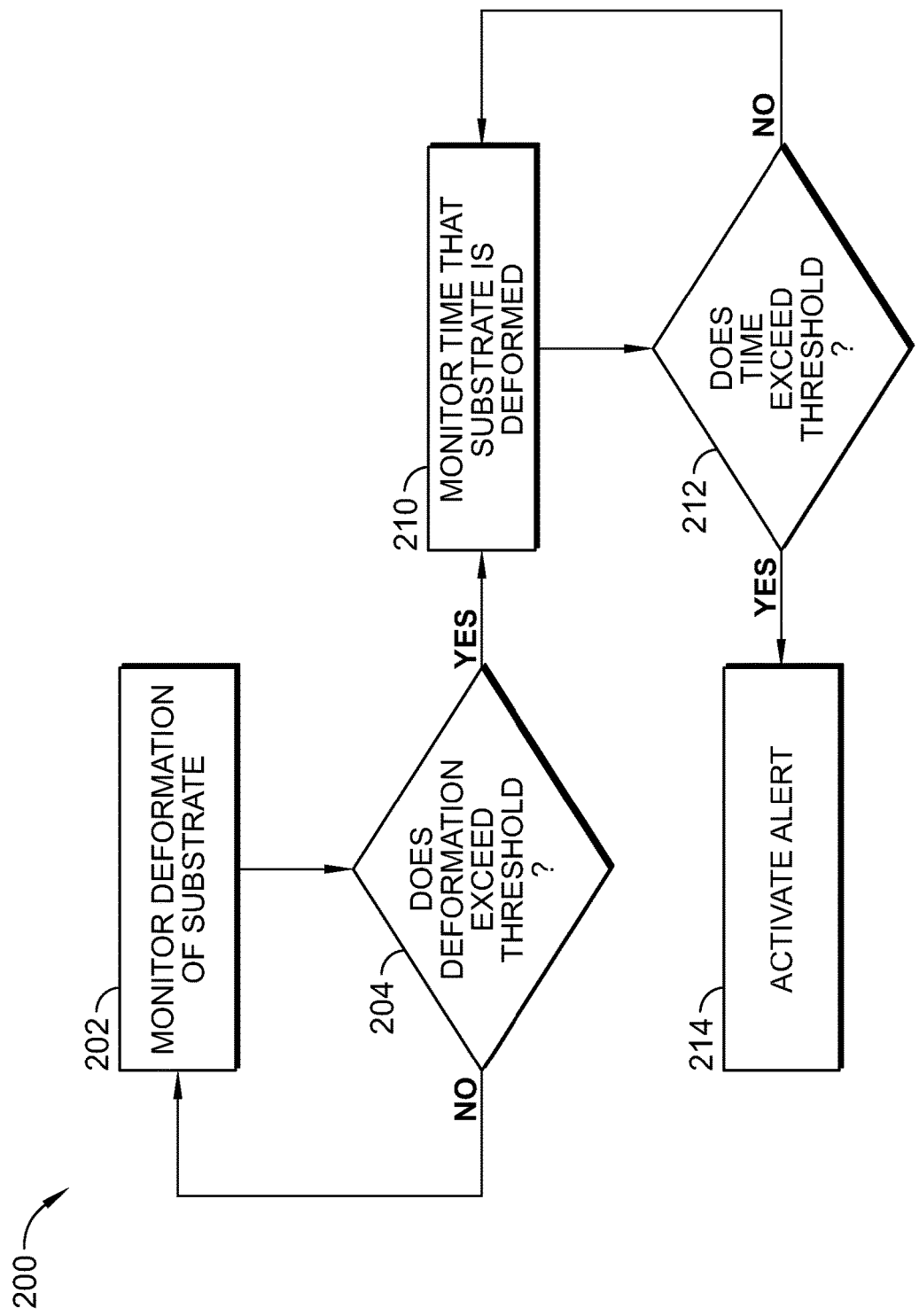
FIG. 10 is a flowchart of a method for detecting skin deformation and a time that the skin is deformed so that an alert can be activated if the skin is deformed for greater than a predetermined time.

FIG. 10 illustrates a method 200 for detecting the development of pressure sores in a patient. The patient is provided with the artificial skin 22 on the patient's healthy skin in areas that may be prone to pressure sores or any other area of interest for that matter. At block 202, the artificial skin 22 detects deformation of the patient's skin, as described above, in the x-axis, the y-axis, and the z-axis. At block 204, the processor 112 determines whether the deformation of the patient's skin exceeds a predetermined threshold. For example, the predetermined threshold may be determined based on the graphs described below. If the deformation of the patient's skin does not exceed the predetermined threshold, the artificial skin 22 continues to monitor deformation, at block 202. If the deformation of the patient's skin does exceed the predetermined threshold, the processor 112, using signals from the timer 122, monitors a time that the patient's skin has been deformed, at block 210. The processor 112, at block 212, determines whether the time that the patient's skin has been deformed exceeds a predetermined threshold. For example, the predetermined threshold may be determined based on the graphs described below. If the deformation time does not exceed the predetermined threshold, the processor 112 continues to monitor the amount of time that the skin is deformed, at block 210. If the deformation time exceeds the predetermined threshold, the processor 112 activates an alert, at block 214.

Figure 11:
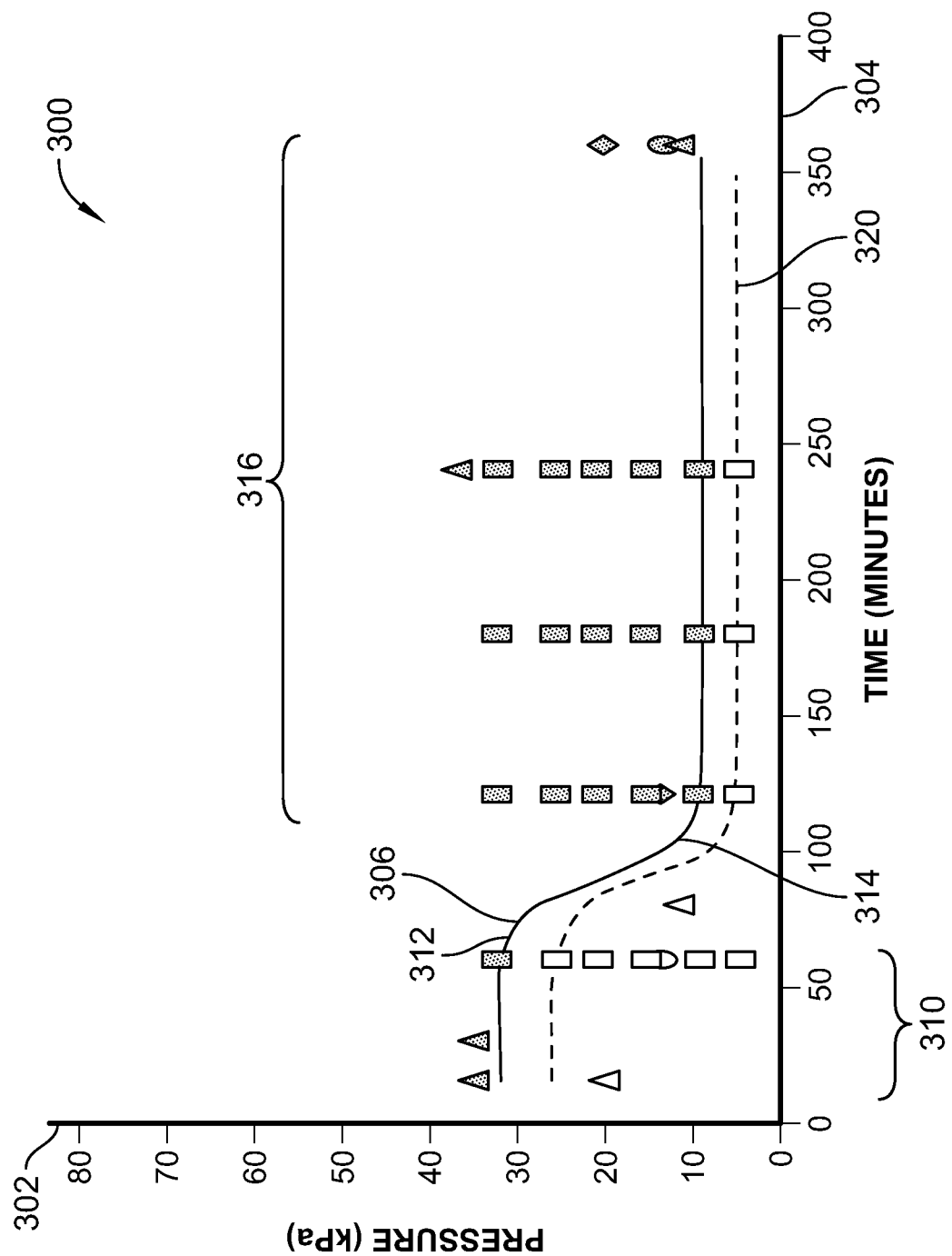
FIG. 11 is a graph of the skin breakdown of rats measured as pressure over time.

FIG. 11 is a graph 300 of the Linder Ganz Breakdown Threshold illustrating pressure on the y-axis 302 over time on the x-axis 304. The graph 300 illustrates the breakdown of rat skin to skin death in line 306 as a function of pressure 302 over time 304. Notably, for a period of time 310, the skin dies at a pressure of over 30 kPa. The period of time is approximately 0-75 minutes. At time 312, approximately 75 minutes, the pressure required for the skin to die decreases at time 314, approximately 100 minutes. For a period of time 316, the pressure required for the skin to die is approximately 10 kPa.

Line 320 illustrates a pressure 302 at which the skin remains healthy as a function of time 304. For the period of time 310, the skin remains healthy at below approximately 30 kPa. The pressure at which the skin remains healthy decreases between time 312 and time 314. For the period of time 316, the skin remains healthy under a pressure of under approximately 10 kPa.

Figure 12:
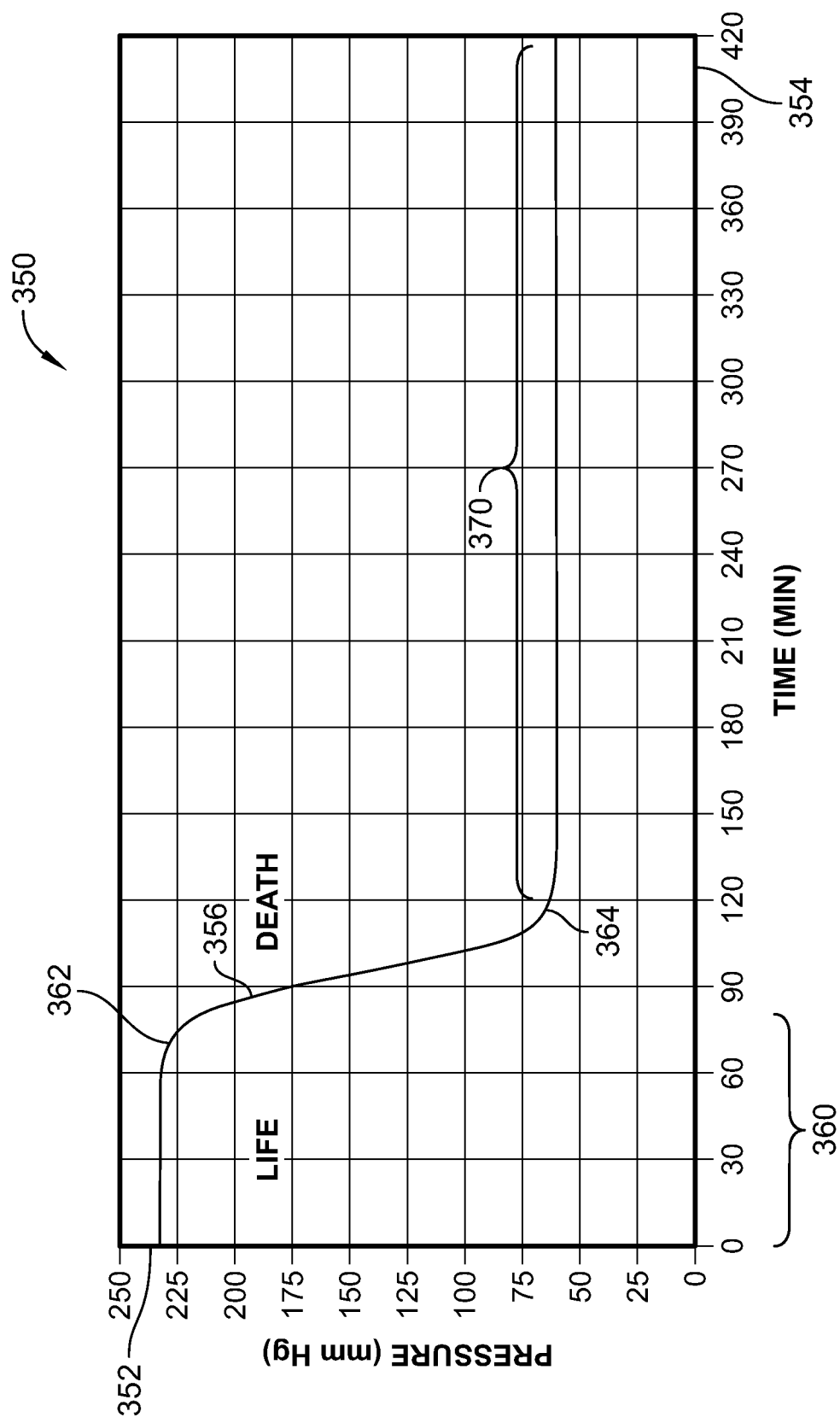
FIG. 12 is a graph of the skin breakdown of humans measured as pressure over time.

FIG. 12 is a graph 350 of the Linder Ganz Breakdown Threshold illustrating pressure on the y-axis 302 over time on the x-axis 304. The graph 350 illustrates the breakdown of human skin to skin death in line 356 as a function of pressure 352 over time 354. For a period of time 360, from 0 minutes to approximately 75 minutes, the human skin begins to breakdown and die at approximately 230 mm Hg. From a time 362, approximately 75 minutes, to a time 364, approximately 100 minutes, the pressure required for the skin to begin breaking down to death decreases. For a period of time 370, after 100 minutes, the pressure for the skin to breakdown to death is approximately 60 mm Hg.

Important lab research suggests that it is not a coincidence that many clinical studies have failed to show any differences in efficacy between 2, 3, 4, and even 8 hour turns of a patient laterally side-to-side. It is assumed that the 2 hour turn is clinically critical as specified in the 2014 International Treatment Guidelines (PPPIA 2014); however, researchers are hopeful that this labor intensive practice can be performed less frequently. The Linder-Ganz study strongly suggests that there is likely to be no difference between 2, 3, and 4 hour turns. Improvements are likely to be seen only with increasing turn frequency as shown in FIGS. 11 and 12.

The artificial skin 22 includes a dressing-based pressure or contact sensor that is situated at a region of concern, most typically the sacrum or other bony prominence of a patient. The artificial skin 22 is used as a contact sensor to determine loading vs. unloading status of that specific site. The sensor may be a simple contact sensor, or may be programmable to a certain threshold pressure that would determine support status of the area of interest on the patient.

The control system 110 includes a timer that is activated once the site is fully loaded. The timer may be programmable to a certain interval based on either the latest research or perhaps on patient status, but generally, this would be intended to substitute for the Q2 turn that is dictated by current practice. When the timer reaches its limit (that is the "not to exceed" interval was met), there is a response that gives an alert to a caregiver, or possibly an intervention intended to rectify the loading situation. The timer 122 is "reset" when area is reloaded after having been unloaded. The device may include an apparatus to unload the area such as an alternating pressure (AP) cycle of a mattress, a lateral pressure rotation (LPR) of a mattress, or an apparatus to increase perfusion or affect temperature at the area of interest.

The artificial skin 22 has the ability to communicate to bed control circuitry and/or to a caregiver in some embodiments, such as via control system 110 described above. The timer 122 resets after each intervention or when reloaded. The control system 110 includes a programmable threshold pressure and a programmable time-out interval. The device may also provide options for intervention at the end of the timer 122.

For the alert to caregiver option, the caregiver may only be alerted when the area of concern has not been unloaded based on the set interval. For example, if the patient were to shift on their own and unload the area of concern, then the timer 122 would be reset. This reduces the number of needed manual turns significantly.

Figure 13:
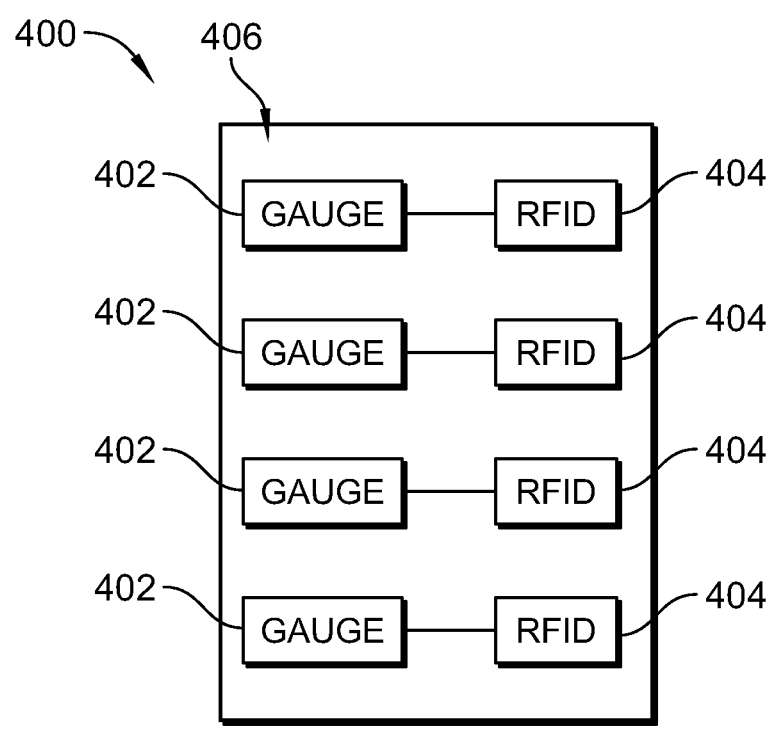
FIG. 13 is a schematic of another embodiment of an artificial skin sensor having multiple gauges and radio-frequency identification tags to detect deformation over time of a patient's skin.

FIG. 13 illustrates an alternative sensor 400 used to measure the dressing deformation, which correlates to tissue deformation and also pressure on the skin. The sensor 400 includes multiple gauges 402 that are connected to passive radio-frequency identification (RFID) tags 404. The deformation of each gauge 402 corresponds to different RFID tag signature.

Each signature corresponds to a different level of deformation because a library of tag signatures may be defined to associate signature to deformation. With an RFID reader located on the mattress or on the bed or even elsewhere in the patient room, the level of deformation of each of the different dressings put on the patient is be detected.

The electronics associated with the RFID reader may also measure the time of each deformation and provide an appropriate warning, e.g. notification to nurse, that deformation over time has reach a level which could potentially generate a pressure ulcer, as described above.

The sensor 400 includes a thick layer of elastomeric material 406 in which several pressure gauges 402 are embedded at different heights to measure electric resistance variation due to sensor deformation. The electric resistance variation is calibrated to be associated with a pressure. The additional gauges 402 located at different heights with different shapes provides additional inputs which facilitate mapping the stress in three dimensions in some embodiments.

The level of tissue deformation over time information is clinical data used to prevent pressure ulcers. An appropriate notification to the nurse enables the nurse to move the patient accordingly. If patient repositioning generates high tissue deformation in other areas, the deformation will be detected and the nurse will be notified according to the present disclosure.

When the terms "approximately," "about," and "substantially" are used herein in connection with a numerical value or geometric term such as "parallel" or "perpendicular," a numeric range of at least ±10% of the given value is intended to be covered and, possibly, even up to ±20% of the given value.

Although this disclosure refers to specific embodiments, it will be understood by those skilled in the art that various changes in form and detail may be made without departing from the subject matter set forth in the accompanying claims.

The invention claimed is:

1. A system for detecting pressure sores comprising:
an artificial skin configured to be coupled to a patient's skin, the artificial skin comprising a substrate and a strain sensor configured to detect deformation of the patient's skin,
a transmitter configured to transmit signals indicative of the deformation of the patient's skin, and
a control system configured to receive the signals from the transmitter, the control system having a timer to track a period of time that the patient's skin is deformed, if the patient's skin is deformed beyond a threshold level of deformation, the control system comparing the period of time that the patient's skin is deformed to a predetermined time, wherein the control system activates an alert if the period of time that the patient's skin is deformed is greater than the predetermined time, wherein the threshold level of deformation is based on a skin type of the patient's skin.

2. The system of claim 1, wherein the artificial skin is configured to be coupled to a patient's healthy skin in regions that are prone to pressure sores.

3. The system of claim 1, wherein the artificial skin includes at least one deformation axis, the strain sensor detecting deformation of the patient's skin along the deformation axis.

4. The system of claim 3, wherein the artificial skin includes:
a first strain sensor to detect deformation of the patient's skin along a first deformation axis, and
a second strain sensor to detect deformation of the patient's skin along a second deformation axis,
wherein the first deformation axis is transverse to the second deformation axis.

5. The system of claim 4, wherein the artificial skin includes a pressure sensor to detect deformation of the patient's skin along a third deformation axis, wherein the third deformation axis is transverse to the first deformation axis and the second deformation axis.

6. The system of claim 5, wherein:
the first deformation axis is substantially perpendicular to the second deformation axis, and
the third deformation axis is substantially perpendicular to the first deformation axis and the second deformation axis.

7. The system of claim 6, wherein:
the first deformation axis and the second deformation axis extend along a surface of the patient's skin, and
the third deformation axis extends substantially perpendicular to a surface of the patient's skin.

8. The system of claim 1, wherein the control system transmits the alert to a remote device.

9. The system of claim 1, wherein the strain sensor includes an elastic strain sensor.

10. The system of claim 9, wherein the elastic strain sensor includes a conductive liquid.

11. The system of claim 10, wherein the conductive liquid includes a conductive metal.

12. The system of claim 11, wherein the conductive liquid includes eutectic gallium-indium.

13. The system of claim 1, wherein the predetermined time is selected based on a period of time required for the skin type of the patient's skin to develop pressure sores.

14. The system of claim 13, wherein the skin type of the patient's skin includes a dryness of the patient's skin.

15. The system of claim 1, wherein the predetermined time is selected based on a location of the patient's skin where the artificial skin is placed.

16. The system of claim 15, wherein the location of the patient's skin includes locations prone to pressure sores.

17. The system of claim 1, wherein the strain sensor detects deformation of the patient's skin in at least one direction.

18. The system of claim 1, wherein the strain sensor detects deformation of the patient's skin in at least two directions.

19. The system of claim 1, wherein the strain sensor detects deformation of the patient's skin in at least three directions.

20. The system of claim 1, wherein deformation of the patient's skin is indicative of pressure sores developing.

* * * * *